United States Patent
Bentley et al.

(10) Patent No.: US 6,602,952 B1
(45) Date of Patent: Aug. 5, 2003

(54) HYDROGELS DERIVED FROM CHITOSAN AND POLY(ETHYLENE GLYCOL) OR RELATED POLYMERS

(75) Inventors: Michael David Bentley, Huntsville, AL (US); Xuan Zhao, Hunstville, AL (US)

(73) Assignee: Shearwater Corporation, Huntsville, AL (US)

( * ) Notice: Subject to any disclaimer, the term of this patent is extended or adjusted under 35 U.S.C. 154(b) by 0 days.

(21) Appl. No.: 09/590,622

(22) Filed: Jun. 8, 2000

Related U.S. Application Data
(60) Provisional application No. 60/138,862, filed on Jun. 11, 1999.

(51) Int. Cl.⁷ .................. C08G 63/48; A01N 43/04; C07H 21/00
(52) U.S. Cl. .................. 524/916; 514/44; 525/54.1; 536/22.1; 536/23.1
(58) Field of Search .................. 536/22.1, 23.1; 514/44; 524/916; 525/54.1

(56) References Cited

U.S. PATENT DOCUMENTS

| | | | |
|---|---|---|---|
| 5,874,500 A | 2/1999 | Rhee et al. | 525/54.1 |
| 5,885,609 A | 3/1999 | Amiji | 424/425 |
| 6,129,761 A | * 10/2000 | Hubbell | 623/11 |
| 6,371,975 B2 | * 4/2002 | Cruise et al. | 606/214 |

FOREIGN PATENT DOCUMENTS

| | | |
|---|---|---|
| EP | 0 486 959 A1 | 5/1992 |
| WO | WO 90/00887 A1 | 2/1990 |

OTHER PUBLICATIONS

Calvo, et al., "Novel Hydrophilic Chitosan–Polyethylene Oxide Nanoparticles as Protein Carriers", *J. Applied Polymer Science*, 1997, pp. 125–132, vol. 63, John Wiley & Sons, Inc.

Bentley, et al., "Reductive Animation Using Poly(ethylene glycol) Acetaldehyde Hydrate Generated in Situ: Applications to Chitosan and Lysozyme", *J. Phar. Sci.*, Nov. 1998, pp. 1446–1449, vol. 87, No. 11.

Harris, et al., "Synthesis and Characterization of Poly(ethylene Glycol) Derivatives", *J. Polymer Sci.*, 1984, pp. 341–352, vol. 22.

MacLaughlin, et al., "Chitosan and Depolymerized Chitosan Oligomers as Condensing Carriers for in Vivo Plasmid Delivery", *J. Cont. Rel.*, 1998, pp. 259–272, vol. 56.

Patel, et al., "pH–Sensitive Swelling and Drug–Release Properties of Chitosan–Poly(ethylene oxide) Semi–interpenetrating Polymer Network", *Am. Chem. Soc.*, 1996, pp. 209–220.

Saito, et al., "Graft Copolymers of Poly(ethylene glycol) (PEG) and Chitosan", *Macromol. Rapid Commun.*, 1997, pp. 547–550, vol. 18.

Schipper, et al., "Chitosans as Absorption Enhancers for Poorly Absorbable Drugs. 1: Influence of Molecular Weight and Degree of Acetylation on Drug Transport Across Human Intestinal Epithelial (Caco–2) Cells", *Phar. Res.*, 1996, pp. 1686–1692, vol. 13, No. 11.

(List continued on next page.)

*Primary Examiner*—Jezia Riley
(74) *Attorney, Agent, or Firm*—Alston & Bird LLP

(57) ABSTRACT

The invention provides a polymeric structure comprising a multifunctional poly(alkylene oxide), such as a poly(ethylene glycol) derivative, covalently cross-linked to a polymer selected from the group consisting of chitosan and conjugates of chitosan and a monofunctional poly(alkylene oxide), such as methoxy poly(ethylene glycol). In aqueous media, the polymeric structure forms a hydrogel that is useful as a drug delivery device, a surgical sealant, or as a delivery system for a medical imaging agent.

89 Claims, 1 Drawing Sheet

Release of lysozyme from PEG-chitosan gel

OTHER PUBLICATIONS

Tozaki, et al., "Chitosan Capsules for Colon–Specific Drug Delivery: Improvement of Insulin Absorption from the Rat Colon", *J. Phar. Sci.,* Sep. 1997, pp. 1016–1021, vol. 86, No. 9.

Zhao, et al., "Novel Degradable Poly(ethylene glycol) Hydrogels for Controlled Release of Protein", *J. Phar. Sci.*, Nov. 1998, pp. 1450–1458, vol. 87, No. 11.

Soane, et al., "Chitosan Molecular Weight and Membrane Transport", *Proceed. Int'l Symp. Control. Rel. Bioact. Mater.*, 1998, pp. 81–82, vol. 25.

Hoffman et al., "Release of Cytokine Receptors From Physical Hydrogels of Plumoronic® Polyethers Grafted to Chitosan Backbones," *Proceed. Int'l. Symp. Control. Rel. Bioact. Mater.*, 1997, p. 126, vol. 24, Controlled Release Society Inc.

\* cited by examiner

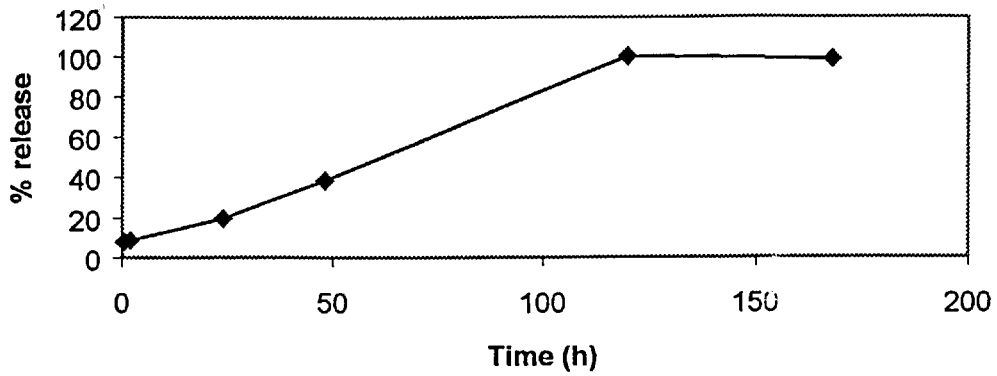
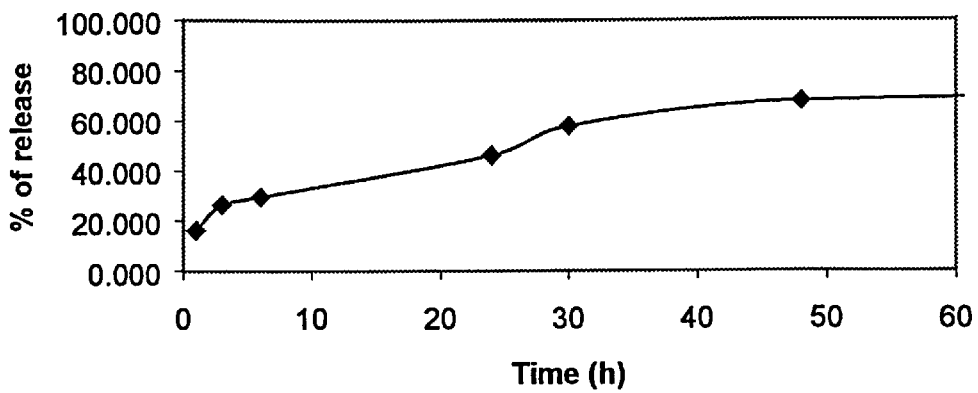

HYDROGELS DERIVED FROM CHITOSAN AND POLY(ETHYLENE GLYCOL) OR RELATED POLYMERS

CROSS-REFERENCE TO RELATED APPLICATIONS

This application claims the benefit of U.S. Provisional Application Ser. No. 60/138,862, filed Jun. 11, 1999, which is incorporated by reference herein in its entirety.

FIELD OF THE INVENTION

This invention relates to hydrogels for biomedical applications.

BACKGROUND OF THE INVENTION

Chitin is an abundant, naturally occurring polymer of N-acetylglucosamine which is present in fungi and in the exoskeletons of crustaceans and insects. When chitin is treated with strong base such as sodium hydroxide, deacetylation occurs to produce the polymer called chitosan. Such chitosan is commonly 80–90% deacetylated. Chitosan is soluble in aqueous acid, but insoluble in water.

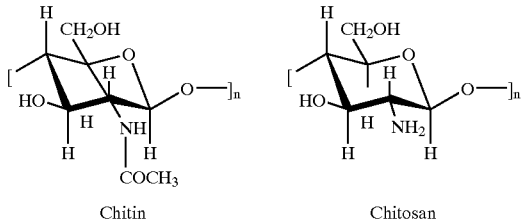

Chitin                Chitosan

Chitosan is of increasing interest in drug delivery. It is known, for example, to enhance transport of hydrophilic drugs such as peptides and proteins across the intestinal epithelial barrier (N. G. Schipper, K. M. Varnum, and P. Artursson, Pharm. Res., 13, 1686–1692, 1996). It has also reported to be useful in both colon delivery (H. Tozaki, et. al, J. Pharm, Sci., 86, 1016–1021, 1997) and nasal delivery of insulin (R. Soane, et. al, Proc. 25th International Symp. on Controlled Release of Bioactive Materials, 1998). Chitosan is also of current interest as a carrier in gene delivery (MacLaughlin, et. al, J. Controlled Release, 56, 259–272, 1998).

Hydrogels, which are cross-linked polymers that swell in water, have potential as drug delivery vehicles. However, many of the hydrogels that have been reported have drawbacks and disadvantages that detract from their use as either drug delivery vehicles or in other biomedical applications. Some cross-linking agents are considered to be toxic and could be problematic if released from the hydrogel in vivo. Some gels are prepared with multiple constituents that can unnecessarily complicate of the preparation of the gels. Some gels are not as stable as desired when used in vivo. It would be desirable to develop new hydrogels that reduce or eliminate some of these drawbacks and disadvantages.

SUMMARY OF THE INVENTION

The invention provides cross-linked polymers of chitosan or alkoxy poly(alkylene oxide) conjugates of chitosan with multifunctionalized poly(alkylene oxide), and methods for their preparation and use. The poly(alkylene oxides) used in the invention are typically poly(ethylene glycols) ("PEGs"), and the discussion below is based on PEG, although it should be recognized that the invention includes other poly(alkylene oxides), including copolymers of ethylene oxide and propylene oxide. These cross-linked structures produce hydrogels in the presence of water that can be useful for, among other things, administering therapeutic agents to humans and other mammals, for the prevention of surgical adhesions, as surgical sealants, as wound dressings, and for the treatment of scars.

In one embodiment, the gels are hydrolytically stable and thus remain intact in vivo for an extended period. In another embodiment, the gel is degradable and provides a water-soluble form of chitosan. The degradable gel can be used for medical imaging applications, in addition to the uses listed above, in which an imaging agent is delivered in vivo.

No cross-linking agents other than chitosan and poly(ethylene glycol) are typically used in the preparation of the hydrogel and the hydrogel can be prepared from chitosan and a single multifunctionalized poly(ethylene glycol). The hydrogel can also be prepared from a chitosan and poly(ethylene glycol) conjugate cross-linked with a multifunctionalized poly(ethylene glycol).

In certain applications, it is advantageous that the chitosan used in forming the cross-linked polymer be present in a form that is water-soluble at or near neutral pH. This invention thus further provides for use of covalently attached monoalkoxy PEG, such as methoxy PEG, on some of the amino groups of the chitosan so that a water-soluble alkoxyPEGylated chitosan can be used for cross-linking with multifunctionalized PEG. The chitosan-PEG conjugate and the cross-linking PEG reagent can thus, in one embodiment, be delivered in solution from separate chambers to form a hydrogel upon mixing of the two solution streams.

Monofunctional PEG moieties, such as alkoxy PEG derivatives, may be attached to chitosan by a variety of methods. For example, PEG can be attached to amino groups on chitosan using an activated PEG carboxylic acid. Such activated PEG carboxylic acids may include acid chlorides, N-succinimidyl esters, 1-hydroxybenzotriazole esters and related activated PEG carboxylic acids. PEG may also be attached to amino groups of the chitosan by a carbonate (urethane) linkage by reaction with PEG chloroformate or an activated PEG carbonate, such as an N-succinimidyl ester or a 1-benzotriazole ester of a PEG carbonate. In another embodiment, a urea linkage may be formed by reaction of chitosan amino groups with an alkoxy PEG isocyanate. Alkoxy PEG may also be attached to chitosan amine groups by reductive amination using sodium cyanoborohydride and a PEG aldehyde, such as mPEG acetaldehyde or mPEG propionaldehyde, or the corresponding aldehyde hydrates and sodium cyanoborohydride. Similar linkages can be formed by reaction of chitosan with PEG activated by appropriate leaving groups such as halide, tosylate, mesylate, or tresylate.

This invention provides methods for cross-linking multifunctional PEG by reaction with amino groups on alkoxy PEG-chitosan conjugates or on chitosan. Such PEG may be difunctional or it may have a greater number of functional groups including, but not limited to, those PEG derivatives prepared from 3-arm, 4-arm, 8-arm or more PEG. Useful activating groups on the termini of the multifunctional PEG are the same as those described above for attaching alkoxy PEG to chitosan. Included are activated derivatives of PEG carboxylic acids, such as N-hydroxysuccinimidyl esters or 1-benzotriazolyl esters. Also included are PEG isocyanates, PEG aldehydes or aldehyde hydrates, and PEG tosylates, mesylates; or tresylates. Cross-linking occurs with the formation of amide, carbamate, or amine linkages to chitosan or an alkoxy PEG-chitosan conjugate.

In certain applications it is advantageous to utilize a hydrogel that breaks down into smaller, water-soluble molecules that can be more readily eliminated from the body. This invention provides for functional groups in the backbone of the cross-linking PEG that can be hydrolyzed at ambient pH or by enzymatic catalysis, or can degrade photochemically. Functional groups that are subject to hydrolysis include, but are not limited to, carboxylate esters, phosphates, sulfates, orthoesters, acetals, certain amides, and certain carbamates. Hydrolytic degradation of the cross-linking PEG moieties results in conversion of the cross-linked chitosan to chitosan that is covalently linked to a PEG, moiety.

In yet another embodiment, the cross-linking PEG can be prepared with a backbone group that is subject to photolytic cleavage. Cinnamylidine esters, for example, dimerize at 313 nm and reversibly cleave at 254 nm. Thus if a PEG having a terminal cinnamylidine ester is linked to chitosan, cross-linking will occur at 313 nm and the process can be reversed at 254 nm.

Biologically active molecules, such as small drug molecules, proteins, peptides, lipids, DNA, carbohydrates, imaging agents, or oligonucleotides, can be physically entrapped in the gel and delivered by diffusion from the hydrogel. Biologically active molecules may also be covalently bound to the amino groups or to the hydroxyl groups of the chitosan moiety of the hydrogel or to a poly(ethylene glycol) moiety.

BRIEF DESCRIPTION OF THE DRAWINGS

Having thus described the invention in general terms, reference will now be made to the accompanying drawings, wherein:

FIG. 1 graphically illustrates the release properties of lysozyme from a PEG chitosan gel; and FIG. 2 graphically illustrates the release properties of BSA from a PEG chitosan gel.

DETAILED DESCRIPTION OF THE INVENTION

The chitosan used in the practice of the invention is a polymer of glucosamine linked at the 1,4-positions. The polymer will normally have a molecular weight range of from about 10,000 to about 1,000,000 daltons and will have from about 0 to about 95 percent of the amino groups acetylated. Preferably, the chitosan has about 0 to about 20 percent of the amino groups acetylated.

The poly(alkylene oxide) derivatives used in the invention are preferably poly(ethylene glycols) ("PEGs"). In its most common form, PEG is a linear polymer terminated at each end with hydroxyl groups:

$$HO-CH_2CH_2O-(CH_2CH_2O)_n-CH_2CH_2-OH$$

wherein n is an integer, such as about 1 to about 2000. This polymer can be represented in brief form as HO-PEG-OH where it is understood that the -PEG- symbol represents the following structural unit:

wherein n is as defined above.

PEG is also commonly used as methoxy PEG-OH, or mPEG in brief, in which one terminus is the relatively inert methoxy group, while the other terminus is a hydroxyl group that is readily modifiable. Due to the presence of the relatively inert methoxy group, mPEG and similar alkoxy poly(alkylene oxides) are often referred to as monofunctional. The mPEG structure is shown below.

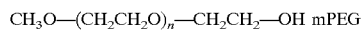

wherein n is as defined above.

PEG is also used in branched forms that can be prepared by addition of ethylene oxide to various polyols, such as glycerol, pentaerythritol and sorbitol. The branched PEGs can be represented in general form as R(-PEG-OH)$_n$ in which R represents the central "core" molecule, such as glycerol or pentaerythritol, and n represents the number of arms. If appropriately functionalized, any of the multifunctional PEGs are suitable for use in the practice of the present invention for cross-linking with chitosan to form hydrogels.

Other poly(alkylene oxides) maybe used in the invention, including copolymers of ethylene oxide and propylene oxide. The copolymers of ethylene oxide and propylene oxide are closely related to PEG in their chemistry, and it is believed that the skilled artisan, when apprised of this disclosure, will understand that these copolymers and other alkylene oxides can be substituted for poly(ethylene glycol) in the preparation of the hydrogels that are described. In a preferred embodiment, the poly(alkylene oxide) has the following structure.

wherein R=H or CH$_3$.

In one embodiment, the chitosan is covalently cross-linked with a multifunctional poly(alkylene oxide) derivative to form a polymeric structure that becomes a hydrogel in the presence of aqueous media. Preferably, the cross-linking poly(alkylene oxide) derivative is a multifunctionalized poly(ethylene glycol). Typically, the PEG derivative will have a molecular weight of about 200 to about 100,000 Da. Multifunctional PEGs have reactive functional groups at two or more termini. These activated PEGs can be bifunctional, having a reactive functional group at each end of the molecule. The activated PEGs can also have 3, 4, or 8 or more arms. Star PEGs having up to about 100 arms are available and these arms can be terminally activated with groups appropriate for the cross-linking reactions described below. All of these various multifunctionalized PEGs are available from Shearwater Polymers, Inc., Huntsville, Ala. The multifunctional poly(ethylene glycol) can be covalently bonded to the chitosan by amide linkages, amine linkages, imine linkages, urea linkages, or carbamate linkages. Carbamate linkages are also referred to as urethane linkages. Preferably, about 1 to about 95 percent of the amine groups on the chitosan are covalently attached to the cross-linking poly(ethylene glycol) by one of the types of linkages described above.

To covalently cross-link poly(ethylene glycol) to chitosan, the activated derivative of the PEG should have a functional group at the terminus that is suitable for reacting with a reactive group on chitosan, such as the amino groups or the alcohol groups. Preferably, the cross-linking PEG has two or more electrophilic functional groups capable of covalently bonding to the nucleophilic amino groups of the chitosan.

An example of a suitable activated derivative for reacting with amino groups is the succinimidyl succinate active ester, CH$_3$O-PEG-O$_2$C—CH$_2$CH$_2$—CO$_2$—NS, where NS is:

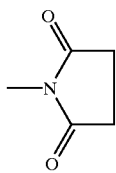

The succinimidyl active ester is a useful compound because it reacts rapidly with amino groups to form an amide linkage (—CO—NH—).

PEG aldehydes are also useful for coupling PEG to chitosan amino groups. When the reaction takes place in the presence of sodium cyanoborohydride, a reductive coupling to form an amine linkage is ensured:

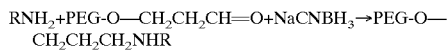

where R is an amine bearing chitosan.

Further, amine reactive functional groups useful in the multifunctional PEGs of the invention are carboxylic acids or esters of carboxylic acids including N-hydroxysuccinimidyl esters or 1-benzotriazolyl esters. Amine reactive functional groups also include aldehydes, aldehyde hydrates, isocyanates, carbonate esters, including N-hydroxysuccinimidyl carbonates and 1-benzotriazolyl carbonates, mesylates, tosylates, or tresylates. It should be readily understood that the poly(ethylene glycol) molecule can have different functional groups present on the same molecule or the same functional groups present on the molecule. A poly(ethylene glycol)molecule having a reactive terminus at each end is sometimes referred to as "bifunctional", or "homobifunctional" if both reactive groups are the same, and as "heterobifunctional" if the two reactive groups are different. It should be understood that the multifunctional poly(ethylene glycol) derivatives of the invention can have, for example, from 2 to about 100 reactive functional groups.

If the PEG polymer backbone does not contain any hydrolytically degradable linkages, the resulting cross-linked PEG-chitosan polymeric hydrogel is hydrolytically stable and, thus, can remain intact in vivo for an extended period. However, it should be recognized that chitosan cross-linked with PEG in which there are no hydrolytically degradable linkages may yet ultimately degrade if enzymes are present that can degrade the chitosan moiety.

In some applications, it is desirable to utilize a hydrogel which breaks down into smaller, water-soluble molecules. This feature is particularly advantageous for in vivo applications because the smaller molecules are more readily eliminated from the body. Thus, such degradable hydrogels are useful for drug delivery. In addition, such degradable hydrogels could be used in imaging or surface coating applications.

To produce a hydrolytically degradable poly(ethylene glycol) that releases a chitosan moiety from the hydrogel, it is advantageous to prepare a poly(ethylene glycol) backbone having a degradable functionality or linkage therein. These degradable functionalities can be, for example, esters, such as carboxylate esters, acetals, orthoesters, phosphates, imines, peptides, sulfates, oligonucleotides, or hydrazones. Choice of a suitable degradable functional group provides some degree of control over the degradation rates of the PEG cross-linking moieties.

In yet another embodiment, the cross-linking PEG can be prepared with a backbone group that is subject to photolytic cleavage. Cinnamylidine esters, for example, dimerize at 313 nm and reversibly cleave at 254 nm. Thus, if a PEG having a terminal cinnamylidine ester is linked to chitosan, cross-linking will occur at 313 nm and the process can be reversed at 254 nm.

The hydrogels of the invention, both degradable and stable, can also be formed by cross-linking poly(ethylene glycol) as described above with a chitosan-poly(ethylene glycol) conjugate. In a preferred embodiment, a monoalkoxy poly(ethylene glycol) is covalently bonded to the chitosan to form a chitosan-alkoxyPEG conjugate prior to cross-linking. Examples of suitable alkoxy groups include, but are not limited to, methoxy, ethoxy, and benzyloxy. The covalent bond between the chitosan and the alkoxy poly(ethylene glycol) typically will be selected from among amide linkages, amine linkages, imine linkages, urea linkages, or carbamate linkages.

Without covalently bonding an alkoxy PEG to the chitosan prior to cross-linking, the chitosan moieties released in the hydrolysis or photolysis product can precipitate if the chitosan is not heavily cross-linked. By initially reacting the chitosan with a monofunctional PEG, such as mPEG, the chitosan moieties released by hydrolytic or photolytic degradation will be water-soluble. As should be understood, other monofunctional poly(alkylene oxides) could be used in the practice of the invention. The monofunctional poly (alkylene oxide) may include degradable linkages in the polymer backbone thereof, as described above in connection with the multifunctional cross-linking poly(alkylene oxides).

Alkoxy PEG moieties can be attached to chitosan by a variety of methods. In a preferred embodiment for preparing the PEG-chitosan conjugate, PEG is attached to amino groups present on the chitosan using an activated PEG carboxylic acid. Such activated PEG carboxylic acids may, include acid chlorides, N-succinimidyl ester, 1-hydroxybenzotriazole esters and related activated PEG carboxylic acids which will be apparent to those skilled in the art. PEG may also be attached to amino groups of the chitosan by a carbamate (urethane linkage) by reaction with PEG chloroformate or an activated PEG carbonate, such as N-succinimidyl ester or a 1-benzotriazole ester of PEG carbonate.

A urea linkage may be formed by reaction of chitosan amino groups with an alkoxy PEG isocyanate. Alkoxy PEG may also be attached to chitosan amine groups by reductive amination using sodium cyanoborohydride and a PEG aldehyde, such as PEG acetaldehyde or PEG propionaldehyde or the corresponding aldehyde hydrates and sodium cyanoborohydride. Similar linkages can be formed by reaction of chitosan with PEG activated by appropriate leaving groups such as tosylate, mesylate, or tresylate.

The cross-linked structures form hydrogels in aqueous media. The solutions of the reactive gel components, including the multifunctionalized poly(ethylene glycol) and the chitosan, can be mixed in the aqueous media to create the hydrogel. A confluent of separate aqueous streams of the reactive gel components can also be injected in vivo or supplied through a spray delivery system, as into the nasal passageways, to create the hydrogel.

Biologically active molecules can be physically entrapped in the gel matrix and then released by diffusion from the polymeric structure. "Biologically active molecule" means a substance that is used in the treatment, cure, prevention, or diagnosis of disease or is otherwise used to enhance physical or mental well being in humans or other animals. These biologically active molecules can include proteins, peptides, lipids, oligonucleotides, DNA, carbohydrates, imaging agents, or small drug molecules. Small drug molecules typically have a molecular weight of less than about 1,000 daltons. These small drug molecules normally are antibacterial agents, antifungals, antiinflammatories, anticancer agents, antiviral agents, antiprotozoan agents, analgesics, antiarrhythmics, antiandrogenics, antihelminthics, antidepressants, or antihypertensive agents.

Cytokines are particularly desirable in the practice of the invention. The cytokine may be, for example, a vascular endothelial growth factor (VEGF), endothelial cell growth factor (ECGF), fibroblast growth factor (FGF), insulin-like growth factor (IGF), bone morphogenic growth factor (BMP), or platelet-derived growth factor (PDGF), epidermal growth factor (EGF), thrombopoietin (TPO), interleukins (IL1–IL15), interferons (IFN), erythropoietin (EPO), ciliary neurotrophic factor (CNTF), colony stimulating factors (G-CSF, M-CSF, GM-CSF), glial cell-derived neurotrophic factor (GDNF), leukemia inhibitory factor(LIF), and macrophage inflammatory proteins (MIP-1a,-1b,-2).

The biologically active molecules can also be independently covalently bonded to one or more of the poly (ethylene glycol) moieties, including branched poly (ethylene glycol) moieties, from which the cross-linked poly(ethylene glycol) and chitosan structure has been prepared. The PEG moieties can be stable or hydrolytically or photochemically degradable. The biologically active molecules can also be covalently bound to the chitosan moiety, if desired.

In addition to being used in vivo, the gels of the invention can be prepared outside the body and used as surgical sealants and for prevention of surgical adhesions, with or without the use of biologically active molecules.

The following examples should be considered in illustration of specific embodiments of the invention, but should not be considered in limitation thereof.

EXAMPLE 1

Preparation of a Hydrogel Formed by Cross-linking mPEG$_{5000}$chitosan with Disuccinimidyl PEG$_{3400}$dipropionate Chitosan (800 mg, MW~75,000 Da, Pronova, Norway) was dissolved in 32 ml of sodium acetate buffer (0.1 M, pH 4). N-Succinimidyl methoxy poly(ethylene glycol) propionate (2.13 g, Shearwater Polymers, Inc. U.S.A.) was dissolved in 15 ml of deionized water and the resulting solution was mixed with the chitosan solution. Phosphate buffer (0.1 M, pH 7, 20 ml) was added drop wise and the resulting solution was shaken overnight at room temperature. Analysis of the resulting solution by capillary electrophoresis demonstrated that no free chitosan remained. Methoxy poly (ethylene glycol) propionic acid, N-hydroxysuccinimide, and salts were removed by ultra filtration (30 KDa cutoff) and the mPEG$_{5000}$chitosan was isolated from the resulting solution by freeze-drying to give the product as a papery, white solid which was water-soluble at physiological pH. The $^1$H nmr spectrum in 50% TFA/D$_2$O (1.93 ppm, s, Ac; 3.07, br s, H-2, deacetylated ring; 3.51 br, PEG backbone; 3.3–4, br m, ring CH and —CH$_2$O— of chitosan; 4.5, C-1 H of acetylated chitosan rings; 4.8, C-1 H of deacetylated chitosan rings) demonstrated that approximately 10% of the glucosamine units in the chitosan were PEGylated.

To 100 mg of mPEG$_{5000}$chitosan derivative dissolved in 10 ml of water was added 200 mg of disuccinimidyl PEG$_{3400}$ dipropionate (Shearwater Polymers) in 10 ml of pH 8 phosphate buffer. A clear gel formed within 2 hours at room temperature.

EXAMPLE 2

Preparation of a Hydrogel by Cross-linking Chitosan with PEG$_{3400}$di(acetaldehyde Diethylacetal)

Chitosan (100 mg) (Carbomer) was dissolved in 25 ml of 2% acetic acid (pH 2.6) and 630 mg of PEG$_{3400}$ di(acetaldehyde diethylacetal) was added. The resulting solution was heated at 75° C. for 20 minutes. After cooling to room temperature, 100 mg of Na(CN)BH$_3$ was added to the resulting solution containing PEG$_{3400}$diacetaldehyde hydrate and the resulting mixture sonicated. A gel formed within 2 minutes. Using HO-PEG-OH and chitosan under the same conditions, no gel formed. No gel formed in the absence of Na(CN)BH$_3$. The gel was washed repeatedly with distilled water, freeze-dried, and re-hydrated and the degree of swelling: [(wt wet-wt dry)/wt dry] was determined to be approximately 33. The product was a soft gel stable at room temperature.

EXAMPLE 3

Preparation of a Chitosan Hydrogel by Cross-linking Chitosan with Disuccinimidyl PEG$_{3400}$dipropionate Chitosan (100 mg, Pronova, CL213) was dissolved in 10 ml of sodium acetate buffer (0.1 M, pH 4). To this solution was added disuccinimidyl PEG$_{3400}$ dipropionate and 8 ml of phosphate buffer (0.1 M, pH 8). A soft clear hydrogel formed within 2 hours.

EXAMPLE 4

Preparation of a Chitosan Hydrogel by Cross-linking Chitosan with 4-arm PEG$_{10,000}$Succinimidyl Carbonate (4-arm PEG 10k SC)

Chitosan (100 mg, Natural Biopolymer, Inc.) was dissolved in 10 ml of sodium acetate buffer (0.1 M, pH 4.0) and 4-arm PEG 10 k SC(500 mg, Shearwater Polymers Inc.) was dissolved in the chitosan solution. A clear, firm gel formed within 2 hours at room temperature.

EXAMPLE 5

Preparation of Hydrolytically Degradable PEG Chitosan Hydrogel

PEG-chitosan conjugate prepared in Example 1 (55 mg) was dissolved in 5 ml of PBS buffer (pH 7.4) to yield a clear, colorless solution. PEG$_{3400}$[—CH$_2$CO$_2$CH(CH$_3$)CH$_2$CO$_2$NS]$_2$ (NS=N-succinimidyl)(10 mg, Shearwater Polymers, Inc., U.S.A.) was added to 1 ml of the PEG chitosan solution with mixing. Gelling was observed in about 2 hours.

EXAMPLE 6

Hydrolytic Degradation of the PEG Chitosan Hydrogel

An approximately 0.5 g sample of the hydrogel prepared in Example 5 was placed in 5 ml of either PBS buffer at pH 7.4 and 37° C. or human plasma at 37° C. and the resulting samples were visually observed. The time required for degradation of the gel as indicated by the formation of a homogeneous solution was 96 hours in buffer and 20 hours in human plasma.

EXAMPLE 7

Enzymatic Degradation of PEG-chitosan Hydrogel by Lysozyme

PEG-chitosan gel (0.15 g) prepared in Example 4 was placed in 2 ml of lysozyme solution (10 mg/ml, pH 7:0) at room temperature (about 23° C.). The gel was totally degraded in 5 days.

EXAMPLE 8

Release of Model Protein Drugs from the Chitosan Gels

BSA and lysozyme were selected as model proteins in the in vitro release study. The proteins were loaded into the gel of Example 4 by rapid stirring. The release studies were performed in a dialysis tube (MWCO 100,000 Da) at 37° C. A pre-weighed gel containing the protein was placed inside a dialysis tube. A buffer solution (50 mM phosphate, 100mM NaCl) was placed outside the tube. At various time intervals, samples were taken for analysis by RP-HPLC. Release profiles are shown in FIGS. 1–2. BSA was released with first order kinetics, while lysozyme followed near zero-order release kinetics.

The invention claimed herein has been described with respect to particular exemplified embodiments. However, the foregoing description is not intended to limit the invention to the exemplified embodiments, and the skilled artisan should recognize that variations can be made within the spirit and scope of the invention as described in the foregoing specification. The invention includes all alternatives, modifications, and equivalents that may be included within the true spirit and scope of the invention as defined by the appended claims.

What is claimed is:

1. A polymeric structure, comprising a multifunctional poly(alkylene oxide) covalently cross-linked to a polymer selected from the group consisting of chitosan and a covalently-bound conjugate of chitosan and a monofunctional poly(alkylene oxide), wherein said multifunctional poly(alkylene oxide) comprises a polymer backbone, said backbone comprising at least one photolytically degradable linkage.

2. A polymeric structure according to claim 1, wherein said multifunctional poly(alkylene oxide) comprises a plurality of amine-reactive functional groups.

3. A polymeric structure according to claim 2, wherein said multifunctional poly(alkylene oxide) comprises about 2 to about 100 amine-reactive functional groups.

4. A polymeric structure according to claim 2, wherein said amine-reactive functional groups are selected from a group consisting of carboxylic acids, carboxylic acid esters, aldehydes, aldehyde hydrates, isocyanates, carbonate-esters, mesylates, tosylates, tresylates, and combinations thereof.

5. A polymeric structure according to claim 2, wherein said amine-reactive functional groups comprise a carboxylic acid ester.

6. A polymeric structure according to claim 5, wherein said carboxylic acid ester is selected from the group consisting of N-hydroxysuccinimidyl esters and 1-benzotriazolyl esters.

7. A polymeric structure according to claim 2, wherein said amine-reactive functional groups comprise a carbonate ester selected from the group consisting of N-hydroxysuccinimidyl carbonates and 1-benzotriazolyl carbonates.

8. A polymeric structure according to claim 1, wherein said multifunctional poly(alkylene oxide) is a multifunctional poly(ethylene glycol).

9. A polymeric structure according to claim 8, wherein said multifunctional poly(ethylene glycol) has a molecular weight from about 200 to about 100,000 Da.

10. A polymeric structure according to claim 1, wherein said multifunctional poly(alkylene oxide) is covalently cross-linked to chitosan.

11. A polymeric structure according to claim 10, wherein said chitosan is a polymer of glucosamine linked at the 1,4-positions having a molecular weight range of about 10,000 Da to about 1,000,000 Da and having from about 0 to about 95% of the amino groups acetylated.

12. A polymeric structure according to claim 11, wherein said chitosan has about 0 to about 20% of the amino groups acetylated.

13. A polymeric structure according to claim 10, wherein said multifunctional poly(alkylene oxide) is covalently cross-linked to chitosan through a linkage selected from the group consisting of amide linkages, amine linkages, imine linkages, urea linkages, carbamate linkages and combinations thereof.

14. A polymeric structure according to claim 10, wherein about 1 to about 95% of the amino groups of the chitosan are covalently attached to the multifunctional poly(alkylene oxide).

15. A polymeric structure according to claim 1, wherein said multifunctional poly(alkylene oxide) is covalently cross-linked to a covalently-bound conjugate of chitosan and a monofunctional poly(alkylene oxide).

16. A polymeric structure according to claim 15, wherein said monofunctional poly(alkylene oxide) comprises a monofunctional poly(ethylene glycol).

17. A polymeric structure according to claim 16, wherein said monofunctional poly(ethylene glycol) comprises a monoalkoxy poly(ethylene glycol).

18. A polymeric structure according to claim 17, wherein the alkoxy group of said monoalkoxy poly(ethylene oxide) is selected from the group consisting of methoxy, ethoxy, and benzyloxy.

19. A polymeric structure according to claim 15, wherein the chitosan and the monofunctional poly(alkylene oxide) are covalently bonded through a linkage selected from the group consisting of amide linkages, amine linkages, imine linkages, urea linkages, and carbamate linkages.

20. A polymeric structure according to claim 15, wherein the functional group of said monofunctional poly(alkylene oxide) is selected from the group consisting of carboxylic acids, carboxylic acid esters, aldehydes, aldehyde hydrates, isocyanates, carbonate esters, mesylates, tosylates, and tresylates.

21. A polymeric structure according to claim 1, wherein said degradable linkage comprises a photolytically degradable linkage selected from the group consisting of cinnamate dimers or cinnamylidine dimers.

22. A polymeric structure, comprising a multifunctional poly(alkylene oxide) covalently cross-linked to a covalently-bound conjugate of chitosan and a monofunctional poly(alkylene oxide).

23. A polymeric structure according to claim 22, wherein said multifunctional poly(alkylene oxide) comprises a plurality of amine-reactive functional groups.

24. A polymeric structure according to claim 23, wherein said multifunctional poly(alkylene oxide) comprises about 2 to about 100 amine-reactive functional groups.

25. A polymeric structure according to claim 23, wherein said amine-reactive functional groups are selected from a group consisting of carboxylic acids, carboxylic acid esters, aldehydes, aldehyde hydrates, isocyanates, carbonate esters, mesylates, tosylates, tresylates, and combinations thereof.

26. A polymeric structure according to claim 23, wherein said amine-reactive functional groups comprise a carboxylic acid ester.

27. A polymeric structure according to claim 26, wherein said carboxylic acid ester is selected from the group consisting of N-hydroxysuccinimidyl esters and 1-benzotriazolyl esters.

28. A polymeric structure according to claim 23, wherein said amine-reactive functional groups comprise a carbonate ester selected from the group consisting of N-hydroxysuccinimidyl carbonates and 1-benzotriazolyl carbonates.

29. A polymeric structure according to claim 22, wherein said multifunctional poly(alkylene oxide) is a multifunctional poly(ethylene glycol).

30. A polymeric structure according to claim 29, wherein said multifunctional poly(ethylene glycol) has a molecular weight from about 200 to about 100,000 Da.

31. A polymeric structure according to claim 22, wherein said multifunctional poly(alkylene oxide) is covalently cross-linked to said conjugate through a linkage selected from the group consisting of amide linkages, amine linkages, imine linkages, urea linkages, carbamate linkages and combinations thereof.

32. A polymeric structure according to claim 22, wherein said monofunctional poly(alkylene oxide) comprises a monofunctional poly(ethylene glycol).

33. A polymeric structure according to claim 32, wherein said monofunctional poly(ethylene glycol) comprises a monoalkoxy poly(ethylene glycol).

34. A polymeric structure according to claim 33, wherein the alkoxy group of said monoalkoxy poly(ethylene oxide) is selected from the group consisting of methoxy, ethoxy, and benzyloxy.

35. A polymeric structure according to claim 22, wherein the chitosan and the monofunctional poly(alkylene oxide) are covalently bound through a linkage selected from the group consisting of amide linkages, amine linkages, imine linkages, urea linkages, and carbamate linkages.

36. A polymeric structure according to claim 22, wherein the functional group of said monofunctional poly(alkylene oxide) is selected from the group consisting of carboxylic acids, carboxylic acid esters, aldehydes, aldehyde hydrates, isocyanates, carbonate esters, mesylates, tosylates, and tresylates.

37. A polymeric structure according to claim 22, wherein said monofunctional poly(alkylene oxide) comprises a polymer backbone, said backbone comprising at least one degradable linkage.

38. A hydrogel, comprising:
  a polymeric structure, comprising a multifunctional poly(alkylene oxide) covalently cross-linked to a polymer selected from the group consisting of chitosan and a covalently-bound conjugate of chitosan and a monofunctional poly(alkylene oxide), wherein said multifunctional poly(alkylene oxide) comprises a polymer backbone, said backbone comprising at least one photolytically degradable linkage; and
  an aqueous medium.

39. A hydrogel according to claim 38, wherein the multifunctional poly(alkylene oxide) comprises a plurality of amine-reactive functional groups.

40. A hydrogel according to claim 39, wherein said amine-reactive functional groups are selected from a group consisting of carboxylic acids, carboxylic acid esters, aldehydes, aldehyde hydrates, isocyanates, carbonate esters, mesylates, tosylates, tresylates, and combinations thereof.

41. A hydrogel according to claim 38, wherein said multifunctional poly(alkylene oxide) is a multifunctional poly(ethylene glycol).

42. A hydrogel according to claim 38, wherein said multifunctional poly(alkylene oxide) is covalently cross-linked to chitosan.

43. A hydrogel according to claim 42, wherein said multifunctional poly(alkylene oxide) is covalently cross-linked to chitosan through a linkage selected from the group consisting of amide linkages, amine linkages, imine linkages, urea linkages, carbamate linkages and combinations thereof.

44. A hydrogel according to claim 38, wherein said multifunctional poly(alkylene oxide) is covalently cross-linked to a covalently-bound conjugate of chitosan and a monofunctional poly(alkylene oxide).

45. A hydrogel according to claim 44, wherein said monofunctional poly(alkylene oxide) comprises a monofunctional poly(ethylene glycol).

46. A hydrogel according to claim 45, wherein said monofunctional poly(ethylene glycol) comprises a monoalkoxy poly(ethylene glycol).

47. A hydrogel according to claim 44, wherein the chitosan and the monofunctional poly(alkylene oxide) are covalently bound through a linkage selected from the group consisting of amide linkages, amine linkages, imine linkages, urea linkages, and carbamate linkages.

48. A hydrogel according to claim 38, further comprising a biologically active molecule entrapped in the polymeric structure.

49. A hydrogel according to claim 48, wherein said biologically active molecule is selected from the group consisting of proteins, peptides, lipids, oligonucleotides, DNA, carbohydrates, imaging agents, and small drug molecules.

50. A hydrogel according to claim 48, wherein said biologically active molecule comprises a small drug molecule having a molecular weight of less than about 1000 Da.

51. A hydrogel according to claim 48, wherein said biologically active molecule comprises a small drug molecule selected from the group consisting of antibacterial, antifungal, antiinflammatory, anticancer, antiviral, antiprotozoan, analgesic, antiarrhythmic, antiandrogenic, antihelminthic, antidepressant, and antihypertensive agents.

52. A hydrogel according to claim 48, wherein said biologically active molecule comprises a cytokine.

53. A hydrogel according to claim 52, wherein the cytokine is selected from the group consisting of vascular endothelial growth factor (VEGF), endothelial cell growth factor (ECGF), fibroblast growth factor (FGF), insulin-like growth factor (IGF), bone morphogenic growth factor (BMP), or platelet-derived growth factor (PDGF), epidermal growth factor (EGF), thrombopoietin (TPO), interleukins (IL1–IL15), interferons (IFN), erythropoietin (EPO), ciliary neurotrophic factor (CNTF), colony stimulating factors, (G-CSF, M-CSF, GM-CSF), glial cell-derived neurotrophic factor (GDNF), leukemia inhibitory factor(LIF), and macrophage inflammatory proteins (MIP-1a,-1b,-2).

54. A hydrogel according to claim 48, wherein said biologically active molecule is covalently bonded to a polymer selected from the group consisting of the multifunctional poly(alkylene oxide), the monofunctional poly(alkylene oxide), and chitosan.

55. A method of forming a hydrogel, comprising:
providing a multifunctional poly(alkylene oxide), wherein the multifunctional poly(alkylene oxide) comprises a polymer backbone, the backbone comprising at least one photolytically degradable linkage;
providing a second polymer component selected from the group consisting of chitosan and a covalently-bound conjugate of chitosan and a monofunctional poly(alkylene oxide); and
mixing the multifunctional poly(alkylene oxide) and the second polymer component in an aqueous medium to form a covalently cross-linked hydrogel.

56. A method according to claim 55, wherein the multifunctional poly(alkylene oxide) comprises a plurality of amine-reactive functional groups.

57. A method according to claim 56, wherein the amine-reactive functional groups are selected from a group consisting of carboxylic acids, carboxylic acid esters, aldehydes, aldehyde hydrates, isocyanates, carbonate esters, mesylates, tosylates, tresylates, and combinations thereof.

58. A method according to claim 55, wherein the multifunctional poly(alkylene oxide) is a multifunctional poly(ethylene glycol).

59. A method according to claim 55, wherein the second polymer component is chitosan.

60. A method according to claim 55, wherein the second polymer component is a covalently-bound conjugate of chitosan and a monofunctional poly(alkylene oxide).

61. A method according to claim 60, wherein the monofunctional poly(alkylene oxide) comprises a monofunctional poly(ethylene glycol).

62. A method according to claim 61, wherein the monofunctional poly(ethylene glycol) comprises a monoalkoxy poly(ethylene glycol).

63. A method according to claim 55, wherein the multifunctional poly(alkylene oxide) and the second polymer component are provided in aqueous solution form.

64. A method according to claim 63, wherein said mixing step comprises mixing aqueous solutions of the multifunctional poly(alkylene oxide) and the second polymer component.

65. A method according to claim 55, further comprising entrapping a biologically active molecule in the hydrogel.

66. A method according to claim 65, wherein the biologically active molecule is selected from the group consisting of proteins, peptides, lipids, oligonucleotides, DNA, carbohydrates, imaging agents, and small drug molecules.

67. A method according to claim 65, wherein said biologically active molecule comprises a small drug molecule having a molecular weight of less than about 1000 Da.

68. A method according to claim 65, wherein said biologically active molecule comprises a small drug molecule selected from the group consisting of antibacterial, antifungal, antiinflammatory, anticancer, antiviral, antiprotozoan, analgesic, antiarrhythmic, antiandrogenic, antihelminthic, antidepressant, and antihypertensive agents.

69. A method according to claim 65, wherein said biologically active molecule comprises a cytokine.

70. A method according to claim 69, wherein the cytokine is selected from the group consisting of vascular endothelial growth factor (VEGF), endothelial cell growth factor (ECGF), fibroblast growth factor (FGF), insulin-like growth factor (IGF), bone morphogenic growth factor (BMP), or platelet-derived growth factor (PDGF), epidermal growth factor (EGF), thrombopoietin (TPO), interleukins (IL1–IL15), interferons (IFN), erythropoietin (EPO), ciliary neurotrophic factor (CNTF), colony stimulating factors (G-CSF, M-CSF, GM-CSF), glial cell-derived neurotrophic factor (GDNF), leukemia inhibitory factor(LIF), and macrophage inflammatory proteins (MIP-1a,-1b,-2).

71. A method according to claim 69, further comprising the step of injecting the hydrogel in vivo.

72. A method according to claim 69, further comprising the step of spraying the hydrogel in vivo.

73. A hydrogel, comprising:
a polymeric structure, comprising a multifunctional poly(alkylene oxide) covalently cross-linked to a covalently-bound conjugate of chitosan and a monofunctional poly(alkylene oxide); and
an aqueous medium.

74. A hydrogel according to claim 73, wherein the multifunctional poly(alkylene oxide) comprises a plurality of amine-reactive functional groups.

75. A hydrogel according to claim 73, wherein said multifunctional poly(alkylene oxide) is a multifunctional poly(ethylene glycol).

76. A hydrogel according to claim 73, wherein said multifunctional poly(alkylene oxide) comprises a multifunctional poly(ethylene glycol).

77. A hydrogel according to claim 76, wherein said monofunctional poly(ethylene glycol) comprises a monoalkoxy poly(ethylene glycol).

78. A hydrogel according to claim 73, further comprising a biologically active molecule.

79. A hydrogel according to claim 78, wherein said biologically active molecule is selected from the group consisting of proteins, peptides, lipids, oligonucleotides, DNA, carbohydrates, imaging agents, and small drug molecules.

80. A method of forming a hydrogen comprising:
providing a multifunctional poly(alkylene oxide);
providing a covalently-bound conjugate of chitosan and a monofunctional poly(alkylene oxide); and
mixing the multifunctional poly(alkylene oxide) and the second polymer component in an aqueous medium to form a covalently cross-linked hydrogel.

81. A method according to claim 80, wherein the multifunctional poly(alkylene oxide) comprises a plurality of amine-reactive functional groups.

82. A method according to claim 80, wherein the multifunctional poly(alkylene oxide) is a multifunctional poly(ethylene glycol).

83. A method according to claim 80, wherein the monofunctional poly(alkylene oxide) comprises a monofunctional poly(ethylene glycol).

84. A method according to claim 83, wherein the monofunctional poly(ethylene glycol) comprises a monoalkoxy poly(ethylene glycol).

85. A method according to claim 80, wherein said mixing step comprises mixing aqueous solutions of the multifunctional poly(alkylene oxide) and the covalently-bound conjugate.

86. A method according to claim 80, further comprising mixing a biologically active molecule with the hydrogel.

87. A method according to claim 86, wherein the biologically active molecule is selected from the group consisting of proteins, peptides, lipids, oligonucleotides, DNA, carbohydrates, imaging agents, and small drug molecules.

88. A method according to claim 80, further comprising the step of injecting the hydrogel in vivo.

89. A method according to claim 80, further comprising the step of spraying the hydrogel in vivo.

* * * * *

UNITED STATES PATENT AND TRADEMARK OFFICE
CERTIFICATE OF CORRECTION

PATENT NO. : 6,602,952 B1
DATED : August 5, 2003
INVENTOR(S) : Bentley et al.

It is certified that error appears in the above-identified patent and that said Letters Patent is hereby corrected as shown below:

<u>Title page,</u>
Item [*] Notice, should read -- Subject to any disclaimer. the term of this patent is extended or adjusted under 35 U.S.C.154(b) by 41 days. --

Signed and Sealed this

Sixth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,602,952 B1
DATED : August 5, 2003
INVENTOR(S) : Bentley et al.

It is certified that error appears in the above-identified patent and that said Letters Patent is hereby corrected as shown below:

Title page,
Item [75], Inventors, in the second inventors address, "Hunstville" should read
-- Huntsville --.

Column 14,
Lines 4-6, "claim 69" should read -- claim 64 --;
Lines 21-22, "multifunctional", both occurences, should read -- monofunctional --;
Line 33, "hydrogen" should read -- hydrogel --.

Signed and Sealed this

Fourteenth Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 6,602,952 B1
DATED : August 5, 2003
INVENTOR(S) : Bentley et al.

It is certified that error appears in the above-identified patent and that said Letters Patent is hereby corrected as shown below:

<u>Title page,</u>
Item [*] Notice, should read -- Subject to any disclaimer. the term of this patent is extended or adjusted under 35 U.S.C.154(b) by 57 days. --

This certificate supersedes Certificate of Correction issued July 6, 2004.

Signed and Sealed this

Twenty-first Day of December, 2004

JON W. DUDAS
*Director of the United States Patent and Trademark Office*